United States Patent [19]

Giordano et al.

[11] Patent Number: 5,053,379

[45] Date of Patent: Oct. 1, 1991

[54] HIGH-ACTIVITY NICKEL CATALYST AND PROCESS FOR PREPARATION THEREOF

[75] Inventors: Nicola Giordano, Messina; Adolfo Parmaliana, Terme Vigliatore; Francesco Frusteri, Messina, all of Italy; Shigeo Sasaki, Ube, Japan; Yasushi Yoshida, Ube, Japan; Kuniaki Nitta, Ube, Japan

[73] Assignee: UBE Industries, Ltd., Ube, Japan

[21] Appl. No.: 594,047

[22] Filed: Mar. 19, 1990

[30] Foreign Application Priority Data

Mar. 20, 1989 [JP] Japan .................................. 1-65965

[51] Int. Cl.$^5$ ............................................. B01J 23/78
[52] U.S. Cl. ............................................. 502/328
[58] Field of Search ............................... 502/328, 337

[56] References Cited

U.S. PATENT DOCUMENTS

| Re. 32,044 | 12/1985 | Atwood et al. | 502/337 X |
|---|---|---|---|
| 2,951,044 | 8/1960 | Wagner et al. | 252/313.2 |
| 3,926,583 | 12/1975 | Rostrup-Nielson | 502/328 |
| 3,928,002 | 12/1975 | Morikawa et al. | 502/328 |
| 3,963,646 | 6/1976 | Teichner et al. | 502/328 X |
| 3,966,391 | 6/1976 | Hindin et al. | 502/302 |
| 3,969,270 | 7/1976 | Lester | 502/328 |
| 4,000,987 | 1/1977 | Okagami et al. | 502/178 X |
| 4,021,185 | 5/1977 | Hindin et al. | 431/7 |
| 4,061,594 | 12/1977 | Michel et al. | 502/303 |
| 4,094,821 | 6/1978 | McVicker et al. | 502/328 |
| 4,160,745 | 7/1977 | Murrell et al. | 502/328 X |
| 4,331,566 | 5/1982 | Bjornson | 502/328 X |
| 4,460,704 | 7/1984 | Twigg | 502/337 X |
| 4,510,039 | 4/1985 | Simone et al. | 502/338 X |

FOREIGN PATENT DOCUMENTS

| 0082222 | 6/1983 | European Pat. Off. . |
|---|---|---|
| 2359116 | 5/1974 | Fed. Rep. of Germany . |
| 2375138 | 7/1978 | France . |
| 46-43363 | 12/1971 | Japan . |
| 49-9312 | 3/1974 | Japan . |
| 55-139836 | 11/1980 | Japan . |
| 55-50080 | 12/1980 | Japan . |
| 60-226414 | 11/1985 | Japan . |
| 63-137754 | 6/1988 | Japan . |
| 63-175642 | 7/1988 | Japan . |
| 63-248444 | 10/1988 | Japan . |
| 2141701 | 1/1985 | United Kingdom . |

OTHER PUBLICATIONS

Report prepared for the United States Department of Energy (DOE/ET/11304-33), "Development of Molten Carbonate Fuel Cell Technology-Technical Progress Report for the Quarter Jul.-Sep., 1984," Work performed under Contract No. DE-AC03-76ET11304.
M. Tarjanyi et al., "Development of Internal Reforming Catalysts for the Direct Fuel Cell," Fuel Cell Seminar, Tucson, Arizona, pp. 177–181 (1985).
M. Saitoh et al., "Effect of Nickel Content and Calcination Temperature On Activity for Methanation of Co and Heat-Resistance of Magnesia-Supported Nickel Catalyst," Report of Environmental Pollution and Resource Institute, vol. 12, No. 3, pp. 1–6 (1983) (with Abstract in English).
H. Terunuma et al., "Methanation by Hydrogenation of $CO_2$-Preparation and Reaction of Ni/MgO Catalyst," Collection of Lectures of Catalyst Discussion Meeting, vol. 52, pp. 38–39 (1983).
H. Masuda et al., "Hydrogenation of CO Over Supported Metal Catalysts (v) Effect of MgO Support on the Surface Reaction of Methanation of CO and $CO_2$," Meikoshi Report, vol. 35, pp. 77–81 (1986) (Abstract in English).
A. Nishida et al., "Properties of Ultrafine Magnesium Oxide Powders Prepared by Vapor-Phase Oxidation," Advances in Ceramics, vol. 21: Ceramic Powder Science, pp. 271–277 (1987).
Chemical Abstracts, vol. 108, No. 20, p. 305, Abstract No. 172265e, May 16, 1988.

*Primary Examiner*—W. J. Shine
*Assistant Examiner*—DOuglas J. McGinty
*Attorney, Agent, or Firm*—Finnegan, Henderson, Farabow, Garrett & Dunner

[57] ABSTRACT

A high-activity nickel type catalyst, which comprises a carrier compound of high-purity ultra-fine single-crystal magnesia having an average particle size of 100 to 2000 Å or a BET specific surface area of 6 to 170 m$^2$/g and metallic nickel or nickel oxide uniformly and thoroughly dispersed on the surface of the carrier in a supported amount of 0.1 to 50% by weight as metallic nickel. The catalyst exhibits a high activity in the steam reforming of hydrocarbons, methanation of synthesis gases, and hydrogenation of cyclic and alicyclic unsaturated hydrocarbons.

12 Claims, No Drawings

HIGH-ACTIVITY NICKEL CATALYST AND PROCESS FOR PREPARATION THEREOF

BACKGROUND OF THE INVENTION

1. Field of the Invention

The present invention relates to a catalyst for use in the steam reforming of hydrocarbons, methanation of synthesis gases, and hydrogenation of cyclic and alicyclic unsaturated hydrocarbons, and a process for the preparation thereof.

More particularly, the present invention relates to a catalyst suitable for the production of starting gases for various synthesis processes such as ammonia synthesis, methanol synthesis, and oxo synthesis, fuel gases such as coal gas, reducing gases for iron manufacture, high-purity hydrogen gases, synthesis gases comprising, as main components, hydrogen, methane, and carbon monoxide and/or carbon dioxide by a steam reforming of hydrocarbons, and a process for the preparation of this catalyst. This catalyst is also suitable for a methanation of synthesis gases comprising, as main components, hydrogen and carbon monoxide and/or carbon dioxide for the production of various gases such as high-purity methane gas and high calory coal gas or for removal of minute amounts of carbon monoxide and carbon dioxide left in a starting gas for the synthesis of ammonia.

2. Description of the Related Art

The present invention relates to a catalyst suitable for a steam reforming of hydrocarbons and methanation of synthesis gases and a process for the preparation of this catalyst. In view of the catalyst activity and from the economical viewpoint, nickel type catalysts are mainly used for these reactions. Most nickel type catalyst commercially available at the present comprise nickel supported on alumina, a refractory oxide (composed mainly of alumina cement), spinel or a similar carrier.

The nickel/alumina type carrier most widely used at present (for example, a catalyst disclosed in Japanese Examined Patent Publication No. 49-9312) is defective in that, since the alumina phase is converted to an α-alumina phase in a high-temperature region and the growth of crystals is advanced, the specific surface area is abruptly decreased, and thus the activity is reduced. To prevent the formation of carbon, a potassium compound is often added to the catalyst of this type, but when the potassium compound-added catalyst is practically used, the potassium compound is scattered in a reaction apparatus, pipes, and the like, to cause a problem of corrosion. Moreover, when the alumina type carrier comes into contact with a high-temperature vapor of an alkali carbonate, a problem of chemical corrosion arises [US. DOE Rep. page 43 (1984), M. Tarjanyi et al, Fuel Cell Seminar, Tucson, Ariz. (USA), page 177 (1985)].

Use of a heat-resistant carrier composed of a composite oxide formed by adding another component to alumina has been attempted. For example, there can be mentioned a carrier obtained by impregnating alumina with lanthanum, lithium or strontium (U.S. Pat. No. 3,966,391, U.S. Pat. No. 4,021,185 and U.S. Pat. No. 4,061,594), a carrier formed by co-precipitating a rare earth metal hydroxide from a rare earth metal salt on alumina (Japanese Patent Application No. 59-80752), a carrier obtained by forming a mixed sol of hydroxides by hydrolyzing an aluminum alkoxide and a lanthanum alkoxide (Japanese Unexamined Patent Publication No. 63-175642), and a carrier obtained by adding magnesia to alumina and calcining the mixture (Japanese Unexamined Patent Publication No. 55-139836). In each of these proposals, a porous carrier is first prepared and an active nickel component is supported in fine pores of this porous carrier by the impregnation method (fine pore impregnation method), and the formed catalyst has an inferior activity. Moreover, the catalyst is defective in that the resistance to chemical corrosion by a high-temperature vapor of an alkali metal carbonate is poor.

Under this background, a nickel/magnesia type catalyst has recently attracted attention, and many reports and patent references have been published [Japanese Examined Patent Publication No. 46-43363, Japanese Examined Patent Publication No. 55-50080, Japanese Unexamined Patent Publication No. 63-137754, Japanese Unexamined Patent Publication No. 63-248444, Report of Environmental Pollution and Resource Institute, 12, No. 3, page 1 (1983), Collection of Lectures at Catalyst Discussion Meeting, 52, page 38 (1983) and Meikoshi Report, 35, page 77 (1986)]. In the catalyst of these reports, magnesia is formed by either the liquid phase method or the thermal decomposition method, and this magnesia is not the high-purity ultra-fine single-crystal magnesia described hereinafter.

SUMMARY OF THE INVENTION

The present invention relates to a nickel/magnesia type catalyst suitable for steam reforming of hydrocarbons and the like and a process for the preparation of this nickel/magnesia type catalyst. The nickel/magnesia type catalyst per se is known, but known techniques concerning this nickel/magnesia catalyst involve various problems. More specifically, (1) the catalyst activity is relatively low and the space-time yield is low, (2) the precipitation of carbon is often caused and the life of the catalyst is short, (3) the heat resistance is low and deactivation occurs, (4) corrosion of a reactor, pipes and the like is caused by scattering of an alkali component, and (5) the resistance to chemical corrosion by a high-temperature vapor of an alkali metal carbonate is low.

The present invention relates to a high activity nickel type catalyst suitable for steam reforming of hydrocarbons and methanation of synthesis gases, which is prepared under specific conditions described below by using high-purity ultra-fine single-crystal magnesia, a nickel compound, and an organic solvent. The catalyst prepared according to the present invention can solve all of the foregoing various problems.

DESCRIPTION OF THE PREFERRED EMBODIMENTS

The catalyst of the present invention and the preparation process thereof will now be described in detail.

High-purity ultra-fine single crystal magnesia (having a purity of at least 99.9%) having an average particle size of 100 to 2000 Å or a BET specific surface area of 6 to 170 $m^2/g$ is used as the starting material of the carrier and, for example, magnesia formed by the gas phase oxidation method in which a vapor of magnesium is oxidized with an oxygen-containing gas in the turbulently dispersed state is preferably used. Magnesia having an average particle size smaller than 100 Å can be prepared, and this magnesia can be used in the present invention. At present, however, the utility of this magnesia is low because the manufacturing cost is high and handling of this powdery magnesia is generally difficult.

If the average particle size exceeds 2000 Å, the specific surface area of the carrier is reduced below 5 m²/g and the catalyst activity is lowered. Accordingly, preferably the average particle size of high-purity ultra-fine single-crystal magnesia is 100 to 2000 Å or a BET specific surface area of 6 to 170 m²/g, especially 300 to 700 Å or a BET specific surface area of 20 to 80 m²/g.

Any nickel compounds soluble in organic solvents and thermally decomposable at temperatures lower than 400° C. can be used as the starting material for the preparation of the catalyst in the present invention. For example, there are preferably used bisacetylacetonatonickel, bisdimethylglyoximatonickel, dicarbonylbistriphenylphosphine nickel, dicarbonylbiscyclopentadienyl nickel, biscyclopentadienyl nickel, acetylene-biscyclopentadienyl nickel, biscycloocotadiene nickel, nickel alkoxides, nickel acetate, nickel nitrate, and hydrates thereof.

Any organic solvents having a water content not higher than 1% and capable of dissolving the foregoing nickel compounds therein can be used as the organic solvent for the preparation of the catalyst in the present invention. For example, there are preferably used alcohols such as methanol, ethanol and propanol, hydrocarbons such as hexane, heptane, cyclohexane and ether, and aromatic hydrocarbons such as benzene, toluene and xylene. From the economical viewpoint, an organic solvent capable of dissolving a large quantity of the nickel compound therein is especially preferred.

By using the foregoing three starting materials, i.e., the high-purity ultra-fine single-crystal magnesia, the nickel compound and the organic solvent, the nickel compound is supported on the surface of magnesia particles by the incipient wetness method to prepare the catalyst. Preferably, the amount supported of the nickel compound is 0.1 to 50% by weight as metallic nickel based on the magnesia carrier. If the amount supported of the nickel compound is smaller than 0.1% by weight, the catalyst activity is low, and if the amount supported of the nickel compound is larger than 50% by weight, the catalyst activity is not increased in proportion to the amount of the nickel compound, and use of such a large amount of the nickel compound is not preferable from the economical viewpoint.

A slurry comprising the magnesia, nickel compound, and organic solvent is dried at 50° to 150° C. to remove the organic solvent. From the economical viewpoint, preferably the organic solvent is recovered and used again. Then, the so-obtained nickel compound-supported carrier is subjected to a thermal decomposition treatment at a relatively low temperature lower than 400° C., in an air current. This treatment temperature is determined in view of the thermal decomposition point of the nickel compound, the thermal decomposition speed of the nickel compound, and safety. If the treatment temperature is higher than 400° C., a strong solid solution of nickel and magnesia is formed, and the subsequent reduction treatment with hydrogen becomes difficult. Then the so-prepared nickel oxide-supported magnesia powder is molded (pelletized) into a granule, tablet, column or ring to obtain a nickel/magnesia (Ni/MgO) catalyst.

To obtain a high catalyst activity by using this Ni/MgO catalyst, preferably the catalyst is subjected to a reduction treatment described below just before actual use. Namely, activation is effected by performing a first reduction treatment at a temperature of 350° to 450° C. and a second reduction treatment at a temperature of 600° to 750° C. in a hydrogen gas current having a hydrogen concentration of 30 to 100%. The flow rate of the hydrogen gas is generally 10 to 100 Nml/min per gram of the catalyst, but as the amount supported of nickel is increased, the flow rate of the hydrogen gas must be increased.

When the catalyst of the present invention is used for the steam reforming reaction and the like, an ordinary reactor such as a tube type flow reactor (continuous flow fixed bed reactor) or a fluidized bed reactor is used and the reaction can be carried out under ordinary conditions. Since the activity of the catalyst of the present invention is very high, a reaction temperature lower than the customarily adopted temperature can be adopted. Moreover, the space velocity (GHSV) can be elevated to a high level, or in the steam reforming reaction, the steam/carbon molar ratio can be reduced.

High-purity ultra-fine single-crystal magnesia particles consist of cubic crystals, and $Mg^{2+}$ ions and $O^{2-}$ ions located at semi-crystal sites are in the activated state as tri-coordinated and unsaturated ions. The finer the magnesia particles, the greater the number $Mg^{2+}$ ions and $O^{2-}$ ions in the state, and this participates directly in the catalyst activity.

Since magnesia is strongly alkaline, it is not necessary to add the alkaline compound usually added to a conventional catalyst, and the rate of carbon formation becomes very low by the existence of magnesia. Even if a formation of carbon occurs, since magnesia is an ultra-fine powder, the formed carbon has a very small particle size, and thus is easily gasified and not accumulated on the catalyst. Further, since magnesia is strongly alkaline, a high resistance to chemical corrosion by a high-temperature vapor of an alkali metal carbonate can be obtained.

Since the nickel compound is supported on the surface of magnesia by using the organic solvent, magnesia does not cause any chemical change such as hydration, the shape and size of magnesia are not changed and the above-mentioned activated state can be maintained after the preparation of the catalyst. Moreover, since the nickel compound is supported by the incipient wetness method, the dispersion of nickel is very good and the surface area of active nickel per unit weight of the catalyst is large.

Furthermore, since nickel oxide (NiO) is formed by thermally decomposing the nickel compound at a relatively low temperature lower than 400° C., free NiO is supported on the surface of magnesia, and at the subsequent reducing step, the reduction can be accomplished at a relatively low temperature. This is one of the advantages gained by the present invention. At the reducing step, the first reduction treatment is carried out at 350° to 450° C. and the second reduction treatment is carried out at 600° to 750° C. A catalyst having a sufficiently high activity can be obtained only by the first reduction treatment but if the second reduction treatment is carried out, the activity is further elevated and the catalyst is stabilized. Although the reason therefor is not clear, it is considered that, since the catalyst is usually used at a temperature higher than 400° C., if the reduction treatment is performed at a higher temperature in advance, good results can be obtained.

The present invention will be now described in detail with reference to the following examples and comparative examples.

EXAMPLES 1 AND 2

To 10 g of high-purity ultra-fine single-crystal magnesia (having an average particle size of 500 Å or a BET specific surface area of 30 m$^2$/g) formed by the gas phase oxidation method was added a solution of bisacetylacetonatonickel in toluene, and the nickel compound was supported by the incipient wetness method and toluene was removed at 90° C. under suction. The dry product was subjected to a thermal decomposition treatment at 400° C. for 6 hours in an air current to decompose bisacetylacetonatonickel completely. When the amount of nickel supported on the so-obtained Ni/MgO type catalyst was determined by the atomic absorption spectroscopy, it was found that the supported amount was 18% by weight as metallic nickel based on magnesia.

The Ni/MgO type catalyst was granulated to a size of 1 to 3 mm and a part (about 1 g) of the granulated catalyst was packed in a usual fixed bed type flow reactor. The first reduction treatment was carried out at a temperature of 400° C. under a pressure of 1 atmosphere for 2 hours while flowing a hydrogen gas having a hydrogen concentration of 100% at a flow rate of 100 Nml/min, and the second reduction treatment was carried out at a temperature of 725° C. under a pressure of 1 atmosphere for 1 hour while flowing a hydrogen gas having a hydrogen concentration of 100% at a flow rate of 100 ml/min. A mixed gas comprising H$_2$O and CH$_4$ at an H$_2$O/CH$_4$ molar ratio of 2.5 was flowed through the reactor at a flow rate of 1 Nl/min under a pressure of 1 atmosphere at a reaction temperature of 625° C. (Example 1) or 800° C. (Example 2). The composition of the gas at the outlet of the reactor was analyzed by the gas chromatography, and the results are shown in Table 1.

TABLE 1

| Example No. | Reaction Temperature (°C.) | Space Velocity GHSV (hr$^{-1}$) | Methane Conversion $C_1$ (%) | Equilibrium State Conversion $C_2$ (%) | $C_1/C_2$ | Space-Time Yield STY (milliomole/g · hr) |
|---|---|---|---|---|---|---|
| Example 1 | 625 | 30,000 | 79.0 | 79 | 1.00 | 363 |
| Example 2 | 800 | 30,000 | 100.0 | 100 | 1.00 | 459 |

EXAMPLES 3 THROUGH 6 AND COMPARATIVE EXAMPLE 1

Ni/MgO type catalysts were prepared in the same manner as described in Example 1 except that the amount supported of nickel was changed to about 0, 0.1, 5, 25 or 50% by weight from 18% by weight. The reduction treatment and catalyst activity test were carried out in the same manner as described in Example 1. The results are shown in Table 2.

TABLE 2

| Example No. | Nickel Supported Amount (% by weight based on MgO) | Methane Conversion $C_1$ (%) | Equilibrium State Conversion $C_2$ (%) | $C_1/C_2$ | Space-Time Yield STY (milliomole/g · hr) |
|---|---|---|---|---|---|
| Comparative Example 1 | 0 | 4.9 | 79 | 0.06 | 24 |
| Example 3 | 0.1 | 45.1 | 79 | 0.57 | 207 |
| Example 4 | 5.0 | 71.0 | 79 | 0.90 | 327 |
| Example 5 | 24.8 | 79.0 | 79 | 1.00 | 363 |
| Example 6 | 49.9 | 79.0 | 79 | 1.00 | 363 |

EXAMPLES 7 THROUGH 9

A catalyst was prepared in the same manner as described in Example 1 except that the average particle size of high-purity ultra-fine single-crystal magnesia was changed to 100 Å (Example 7), 1000 Å (Example 8) or 2000 Å (Example 9) from 500 Å. The reduction treatment and the catalyst activity test were carried out in the same manner as described in Example 1. The results are shown in Table 3.

TABLE 3

| Example No. | Average Particle Size (Å) of Starting Magnesia | Methane Conversion $C_1$ (%) | Equilibrium Conversion $C_2$ (%) | $C_1/C_2$ | Space-Time Yield STY (millimole/g · hr) |
|---|---|---|---|---|---|
| Example 7 | 100[1] | 79.0 | 79 | 1.00 | 363 |
| Example 8 | 1000[2] | 73.9 | 79 | 0.94 | 339 |
| Example 9 | 2000[3] | 70.1 | 79 | 0.89 | 321 |

[1]BET specific surface area = 160 m$^2$/g
[2]BET specific surface area = 16 m$^2$/g
[3]BET specific surface area = 8 m$^2$/g

COMPARATIVE EXAMPLES 2 AND 3

Catalysts were prepared in the same manner as described in Example 1 except that commercially available liquid phase method magnesia (having an average particle size of 500 Å or a BET specific surface area of 30 m$^2$/g) or commercially available lithium aluminate (having an average particle size of 500 Å or a BET specific surface area of 30 m$^2$/g) was used instead of the high-purity ultra-fine single-crystal magnesia having an average particle size of 500 Å, which was used in Example 1. The reduction treatment and the catalyst activity test were carried out in the same manner as described in Example 1. The results are shown in Table 4.

TABLE 4

| Example No. | Starting Carrier | Methane Conversion $C_1$ (%) | Equilibrium Conversion $C_2$ (%) | $C_1/C_2$ | Time-Space Yield STY (millimole/g · hr) |
|---|---|---|---|---|---|
| Comparative Example 2 | liquid phase method magnesia | 77.0 | 79 | 0.97 | 354 |

TABLE 4-continued

| Example No. | Starting Carrier | Methane Conversion $C_1$ (%) | Equilibrium Conversion $C_2$ (%) | $C_1/C_2$ | Time-Space Yield STY (millimole/g · hr) |
|---|---|---|---|---|---|
| Comparative Example 3 | commercially available lithium aluminate | 76.2 | 79 | 0.96 | 348 |

EXAMPLES 10 THROUGH 15 AND COMPARATIVE EXAMPLES 4 AND 5

Catalysts were prepared in the same manner as described in Example 1 except that an ethanol solution of bisdimethylglyoxymatonickel (Example 10), an ether solution of biscyclopentadienyl nickel (Example 11), a heptane solution of acetylene-biscyclopentadienyl nickel (Example 12), an isopropanol solution of a nickel alkoxide (Example 13), an ethanol solution of nickel acetate (Example 14), an ethanol solution of nickel nitrate (Example 15), a toluene solution of bisacetylacetonatonickel (Comparative Example 4) or an aqueous solution of nickel nitrate (Comparative Example 5) was used instead of the toluene solution of bisacetylacetonatonickel used in Example 1 and the thermal decomposition was carried out under conditions described below. The reduction treatment and the catalyst activity test were carried out in the same manner as described in Example 1. The results are shown in Table 5.

TABLE 5

| Example No. | Nickel Compound and Solvent used for Preparation of Catalyst | Thermal Decomposition Conditions temperature (°C.) | time (hours) | Methane Conversion (%) | Space-Time Yield STY (millimole/g · hr) |
|---|---|---|---|---|---|
| Example 10 | bisdimethylglyoxy-matonickel-ethanol | 350 | 6 | 78.9 | 363 |
| Example 11 | biscyclopentadienyl nickel-ether | 350 | 6 | 79.0 | 363 |
| Example 12 | acetylene-biscyclo-pentadienyl nickelheptane | 300 | 6 | 78.8 | 362 |
| Example 13 | nickel alkoxide-iso-propanol | 250 | 6 | 79.0 | 363 |
| Example 14 | nickel acetate-ethanol | 400 | 6 | 78.8 | 362 |
| Example 15 | nickel nitrate-ethanol | 400 | 6 | 79.0 | 363 |
| Comparative Example 4 | bisacetylacetonato-nickel-toluene | 500 | 6 | 39.8 | 183 |
| Comparative Example 5 | nickel acetate-water | 400 | 6 | 35.0 | 161 |

EXAMPLES 16 THROUGH 18

Catalysts were prepared in the same manner as described in Example 1 except that the temperature of the first reduction treatment was changed to 350° C. from 400° C. (Example 16), the temperature of the second reduction treatment was changed to 600° C. from 725° C. (Example 17), or the conditions of the first reduction treatment were changed to a hydrogen concentration of 30%, a hydrogen gas flow rate of 200 Nml/min, a temperature of 350° C., a pressure of 1 atmosphere and a time of 4 hours from the hydrogen concentration of 100%, the hydrogen gas flow rate of 100 Nml/min, the temperature of 400° C., the pressure of 1 atmosphere and the time of 2 hours and the conditions of the second reduction treatment were changed to a hydrogen concentration of 30%, a hydrogen gas flow rate of 200 Nml/min, a temperature of 600° C., a pressure of 1 atmosphere and a time of 2 hours from the hydrogen concentration of 100%, the hydrogen gas flow rate of 100 Nml/min, the temperature of 725° C., the pressure of 1 atmosphere and the time of 1 hour (Example 18). The catalyst activity test was carried out in the same manner as described in Example 1. The results are shown in Table 6.

TABLE 6

| | Reduction Treatment Conditions | | | | | | | | | |
|---|---|---|---|---|---|---|---|---|---|---|
| | First | | | | Second | | | | | Space-time |
| Example No. | hydrogen concentration (%) | hydrogen gas flow rate (Nml/min) | temperature (°C.) | time (hrs) | hydrogen concentration (%) | hydrogen gas flow rate (Nml/min) | temperature (°C.) | time (hrs) | Methane Conversion (%) | Yield STY (millimole/ g · hr) |
| Example 16 | 100 | 100 | 350 | 2 | 100 | 100 | 725 | 1 | 78.3 | 357 |
| Example 17 | 100 | 100 | 400 | 2 | 100 | 100 | 600 | 1 | 76.9 | 354 |
| Example 18 | 30 | 200 | 350 | 4 | 30 | 200 | 600 | 2 | 74.8 | 345 |

EXAMPLE 19

A catalyst was prepared in the same manner as described in Example 1 except that the amount supported of nickel was changed to 2% by weight from 18% by weight and the hydrogen gas flow rate was changed to 15 Nml/min from 100 Nml/min at the first and second reduction treatments. The catalyst activity test was carried out in the same manner as described in Example 1. The results are shown in Table 7.

TABLE 7

| Example No. | Reduction Treatment Conditions | | | | | | | | Methane Conversion (%) | Space-time Yield STY (millimole/g · hr) |
|---|---|---|---|---|---|---|---|---|---|---|
| | First | | | | Second | | | | | |
| | hydrogen concentration (%) | hydrogen gas flow rate (Nml/min) | temperature (°C.) | time (hrs) | hydrogen concentration (%) | hydrogen gas flow rate (Nml/min) | temperature (°C.) | time (hrs) | | |
| Example 19 | 100 | 15 | 400 | 2 | 100 | 15 | 725 | 1 | 65.0 | 297 |

Note
The amount supported of nickel in the catalyst was 2% by weight.

COMPARATIVE EXAMPLES 6 THROUGH 8

Catalysts were prepared in the same manner as described in Example 1 except that the temperature of the first reduction treatment was changed to 500° C. from 400° C. (Comparative Example 6), the temperature of the second reduction treatment was changed to 800° C. from 725° C. (Comparative Example 7), or the temperature of the first reduction temperature was changed to 500° C. from 400° C. and the temperature of the second reduction treatment was changed to 800° C. from 725° C. (Comparative Example 8). The catalyst activity test was carried out in the same manner as described in Example 1. The results are shown in Table 8.

EXAMPLES 22 AND 23 COMPARATIVE EXAMPLES 12 THROUGH 15

By using about 1 g of the Ni/MgO catalyst of Example 1, the Ni/MgO catalyst of comparative Example 2 or the Ni/LiAlO$_2$ catalyst of Comparative Example 3, the reduction treatment was carried out in a fixed bed type reactor charged with the catalyst in the same manner as described in Example 1, and a mixed gas having an H$_2$/CO molar ratio of 3.0 was flowed at a rate of 200 Nml/min under a pressure of 1 atmosphere and the reaction was carried out at 300° or 400° C. The results are shown in Table 10.

TABLE 8

| Example No. | Reduction Treatment Conditions | | | | | | | | Methane Conversion (%) | Space-time Yield STY (millimole/g · hr) |
|---|---|---|---|---|---|---|---|---|---|---|
| | First | | | | Second | | | | | |
| | hydrogen concentration (%) | hydrogen gas flow rate (Nml/min) | temperature (°C.) | time (hrs) | hydrogen concentration (%) | hydrogen gas flow rate (Nml/min) | temperature (°C.) | time (hrs) | | |
| Comparative Example 6 | 100 | 100 | 500 | 2 | 100 | 100 | 725 | 1 | 43.0 | 198 |
| Comparative Example 7 | 100 | 100 | 400 | 2 | 100 | 100 | 800 | 1 | 40.8 | 189 |
| Comparative Example 8 | 100 | 100 | 500 | 2 | 100 | 100 | 800 | 1 | 37.4 | 171 |

EXAMPLES 20 AND 21 AND COMPARATIVE EXAMPLES 9 THROUGH 12

The catalyst activity test was carried out in the same manner as described in Example 1 except that 1 g of the Ni/MgO catalyst of Example 1, the Ni/MgO catalyst formed by using liquid phase method magnesia, which was used in Comparative Example 2 or the Ni/AlO$_2$ catalyst formed by using lithium aluminate, which was used in Comparative Example 3, was used, and a mixed gas having and H$_2$O/CH$_4$ molar ratio of 2.5 was fed at a rate of 5 or 10 Nl/min, which was adopted instead of 1 Nl/min. The results are shown in Table 9.

| Example No. | Catalyst | Reaction | Reaction Temperature (°C.) | Conversion (%) | Space-Time Yield STY (millimole/g · hr) |
|---|---|---|---|---|---|
| Example 22 | 18% Ni/MgO of present invention | methanation | 300 | 90.0 | 121 |
| Example 23 | 18% Ni/MgO of present invention | methanation | 400 | 100.0 | 134 |
| Comparative Example 12 | 18% Ni/liquid phase method MgO | methanation | 300 | 69.1 | 92 |
| Comparative Example 13 | 18% Ni/liquid phase | methanation | 400 | 78.2 | 105 |

TABLE 9

| Example No. | Catalyst | Space Velocity GHSV (hr$^{-1}$) | Methane Conversion C$_1$ (%) | Equilibrium Conversion C$_2$ (%) | C$_1$/C$_2$ | Space-Time Yield STY (millimole/g · hr) |
|---|---|---|---|---|---|---|
| Example 20 | 18% Ni/MgO of present invention | 150000 | 70.4 | 79 | 0.89 | 2694 |
| Example 21 | 18% Ni/MgO of present invention | 300000 | 58.2 | 79 | 0.74 | 4454 |
| Comparative Example 9 | 18% Ni/liquid phase method MgO | 150000 | 48.0 | 79 | 0.61 | 1837 |
| Comparative Example 10 | 18% Ni/liquid phase method MgO | 300000 | 29.4 | 79 | 0.37 | 2250 |
| Comparative Example 11 | 18% Ni/LiAlO$_2$ | 150000 | 11.0 | 79 | 0.14 | 421 |
| Comparative Example 12 | 18% Ni/LiAlO$_2$ | 300000 | 2.5 | 79 | 0.03 | 176 |

TABLE 10-continued

| Example No. | Catalyst | Reaction | Reaction Temperature (°C.) | Conversion (%) | Space-Time Yield STY (millimole/g · hr) |
|---|---|---|---|---|---|
| Comparative Example 14 | method MgO 18% Ni/LiAlO$_2$ | methanation | 300 | 43.5 | 59 |
| Comparative Example 15 | 18% Ni/LiAlO$_2$ | methanation | 400 | 57.4 | 76 |

Note, in all of the foregoing examples, the formation of carbon on the catalyst was not observed, and the specific surface area of the catalyst was not changed by the reaction.

The present invention relates to a catalyst suitable for a steam reforming of hydrocarbons and methanation of synthesis gases, and a process for the preparation of this catalyst. According to the present invention, the following effects can be obtained. Namely, (1) the catalyst activity is high and the space-time yield is very high, and this effect is especially conspicuous when the reaction temperature is relatively low or the space velocity is high; (2) the formation of carbon is not observed and the life of the catalyst is long; (3) the heat resistance is high and deactivation is not caused; (4) scattering of an alkali does not occur and corrosion of a reactor and pipes is prevented; and (5) chemical corrosion by a high-temperature vapor of an alkali metal carbonate is not caused.

We claim:

1. A high-activity nickel type catalyst, which comprises a carrier composed of high-purity ultra-fine single-crystal magnesia having an average particle size of 100 to 2000 Å or a BET specific surface area of 6 to 170 m$^2$/g and a metallic nickel or nickel oxide uniformly and thoroughly dispersed on the surface of the carrier in a supported amount of 0.1 to 50% by weight as metallic nickel.

2. A catalyst as claimed in claim 1, wherein the high-purity ultra-fine single-crystal magnesia is that magnesia that is formed by a gas phase oxidation method in which a vapor of magnesium is oxidized with an oxygen-containing gas in a turbulently dispersed state.

3. A catalyst as claimed in claim 1, wherein the high-purity ultra-fine single-crystal magnesia has an average particle size of 300 to 700 Å or a BET specific surface area of 20 to 80 m$^2$/g.

4. A catalyst as claimed in claim 1, which is in a shape of one of a granule, tablet, column and ring.

5. A catalyst as claimed in claim 1, in a reduced state.

6. A process for preparation of a high-activity nickel type catalyst, which comprises mixing high-purity ultra-fine single-crystal magnesia and a nickel compound with an organic solvent, dispersing and supporting the nickel compound uniformly and thoroughly onto the surface of the magnesia as a carrier by an incipient wetness method, removing the organic solvent, and thermally decomposing the nickel compound as the precursor at a relatively low temperature lower than 400° C. in an air current to effect activation.

7. A process according to claim 6, wherein the high-purity ultra-fine single-crystal magnesia is one having an average particle size of 100 to 2000 Å or a BET specific surface area of 6 to 170 m$^2$/g and is formed by a gas phase oxidation method comprising oxidizing a vapor of magnesium with an oxygen-containing gas in a turbulently dispersed state.

8. A process according to claim 6, wherein the nickel compound as the precursor is selected from bisacetylacetonato-nickel, bis-dimethylglyoximatonickel, dicarbonyl-bis-triphenylphosphine nickel, bis-cyclopentadienyl nickel, acetylene-bis-cyclopentadienyl nickel, bis-cyclooctadiene nickel, nickel alkoxides, nickel acetate, nickel nitrate, and hydrates thereof.

9. A process according to claim 6, wherein the organic solvent is selected from alcohols and aliphatic, alicyclic and aromatic hydrocarbons.

10. A process according to claim 9, wherein the organic solvent has a water content of not higher than 1%.

11. A process for the reparation of a high-activity nickel type catalyst, which comprises mixing high-purity ultra-fine single-crystal magnesia and a nickel compound with an organic solvent, dispersing and supporting the nickel compound uniformly and thoroughly onto the surface of the magnesia as a carrier by an incipient wetness method, removing the organic solvent, thermally decomposing the nickel compound as the precursor at a temperature lower than 400° C. in an air current sufficient to effect activation, molding the mixture into a pellet, and activating by treating said pellet to a first reduction treatment at at temperature of 350° to 450° C. and then a second reduction treatment at at temperature of 600° to 750° C. in a hydrogen gas current having a hydrogen concentration 30 to 100%.

12. A process according to claim 11, wherein the mixture is molded into a pellet of a shape of one of a granule, tablet, column and ring.

* * * * *

UNITED STATES PATENT AND TRADEMARK OFFICE
CERTIFICATE OF CORRECTION

PATENT NO. : 5,053,379
DATED : October 1, 1991
INVENTOR(S) : Nicola Giordano, et al It is certified that error appears in the above-indentified patent and that said Letters Patent is hereby corrected as shown below:

On the Title Page, please correct the serial number to read --07/495,047--.

On the Title Page, Item [57], line 2, change "compound" to --composed--.

Column 12, line 34, change "reparation" to --preparation--.

Signed and Sealed this

Twelfth Day of July, 1994

Attest:

BRUCE LEHMAN

*Attesting Officer*     *Commissioner of Patents and Trademarks*